United States Patent [19]

Yagi et al.

[11] Patent Number: 5,282,854
[45] Date of Patent: Feb. 1, 1994

[54] FLUORINE-CONTAINING BLOCK COPOLYMER AND ARTIFICIAL LENS COMPRISING THE SAME

[75] Inventors: Toshiharu Yagi; Nobuhiko Tsuda; Tsuyoshi Noguchi; Kohsaku Sakaguchi; Yoshito Tanaka; Masayoshi Tatemoto, all of Osaka, Japan

[73] Assignee: Daikin Industries Ltd., Osaka, Japan

[21] Appl. No.: 959,426

[22] Filed: Oct. 13, 1992

Related U.S. Application Data

[63] Continuation of Ser. No. 891,915, Jun. 1, 1992, abandoned, which is a continuation of Ser. No. 595,475, Oct. 11, 1990, abandoned.

[30] Foreign Application Priority Data

Oct. 11, 1989 [JP] Japan ................... 1-265982

[51] Int. Cl.$^5$ ............................................. A61F 2/16
[52] U.S. Cl. ........................................ 623/6; 523/105
[58] Field of Search ........... 623/6; 351/160 H, 160 R; 523/105

[56] References Cited

U.S. PATENT DOCUMENTS

| | | |
|---|---|---|
| 3,929,934 | 12/1975 | Moore et al. |
| 4,155,953 | 5/1979 | Tatemoto et al. |
| 4,166,255 | 8/1979 | Graham .................. 351/160 H |
| 4,652,592 | 3/1987 | Kawashima et al. .......... 525/281 X |
| 4,806,382 | 2/1989 | Goldberg et al. .................. 623/6 |

*Primary Examiner*—Randall L. Green
*Assistant Examiner*—Mary Beth Jones
*Attorney, Agent, or Firm*—Birch, Stewart, Kolasch & Birch

[57] ABSTRACT a fluorine-containing block copolymer comprising at least one soft segment which comprises chlorotrifluoroethylene and vinylidene fluoride and at least one hard segment which comprises a fluorine-containing crystalline polymer, which copolymer has good flexibility and transparency and useful as a material for an artificial lens.

7 Claims, 1 Drawing Sheet

FIGURE
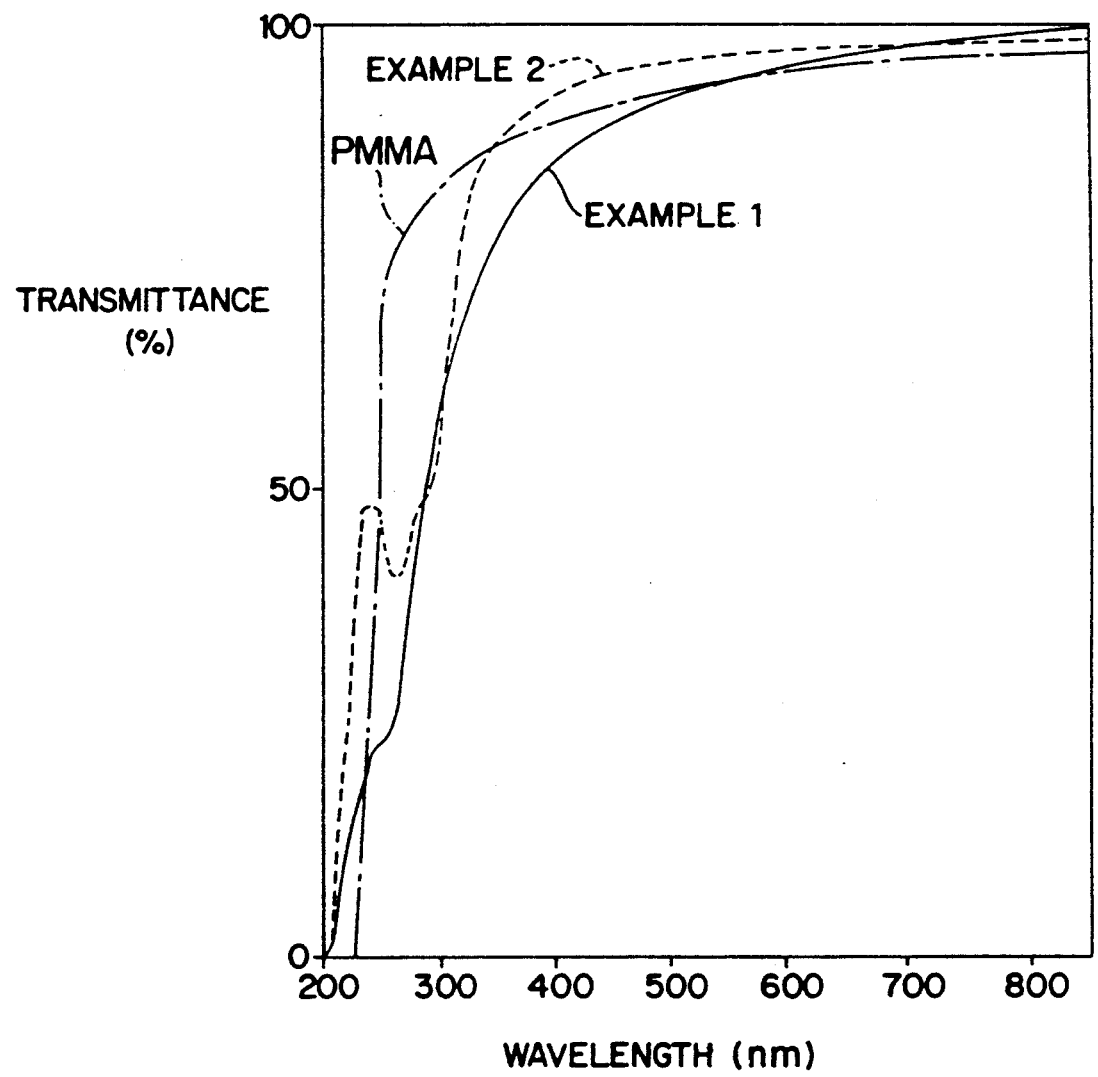

FLUORINE-CONTAINING BLOCK COPOLYMER AND ARTIFICIAL LENS COMPRISING THE SAME

This application is a continuation of copending application Ser. No. 07/891,915, filed on Jun. 1, 1992, which is a continuation of application Ser. No. 07/595,475 filed on Oct. 11, 1990, both now abandoned, the entire contents of which are hereby incorporated by reference.

BACKGROUND OF THE INVENTION

1. Field of the Invention

The present invention relates to a fluorine-containing block copolymer and an artificial lens comprising the same. More particularly, the present invention relates to a fluorine-containing block copolymer which comprises at least one soft segment and at least one hard segment and an artificial lens which comprises said block copolymer.

2. Description of the Related Art

An artificial lens made of polymethyl methacrylate (PMMA) is commercially available and used. Since PMMA is a hard resin, an incisure of at least 7 mm length is necessary to insert the PMMA artificial lens in an eye. As the incisure is smaller the distortion of an visual image is smaller after surgery. Therefore, the incisure of at least 7 mm length is not preferable. In case of resurgery for replacing the artificial lens, it is difficult to remove the used artificial lens since many cells adhere to the surface of the PMMA lens. In addition, since a glass transition temperature ($T_g$) of PMMA is 123° C., it is impossible to sterilize the lens with steam, and the PMMA lens is sterilized with ethylene oxide (EO) gas. However, since residual EO gas tends to cause inflammation, it is necessary to remove the EO gas, but it is troublesome since PMMA easily absorbs the EO gas.

To overcome the above problems of the PMMA artificial crystalline lens, a fluorine-containing block copolymer Daiel Thermo (trade mark) T 530 is proposed. This block copolymer comprises vinylidene fluoride/tetrafluoroethylene/hexafluoropropylene blocks and ethylene/tetrafluoroethylene blocks. However, Daiel Thermo T 530 has a small refractive index of 1.357, its application is limited.

SUMMARY OF THE INVENTION

One object of the present invention is to provide a novel block copolymer which is suitable as a material for an artificial lens.

Another object of the present invention is to provide a soft and flexible artificial lens which can be sterilized with steam and folded when inserted in the eye, and on which little or no proteins adhere, have a larger refractive index and good transparency.

According to the present invention, there are provided a fluorine-containing block copolymer comprising at least one soft segment which comprises chlorotrifluoroethylene and vinylidene fluoride and at least one hard segment which comprises a fluorine-containing crystalline polymer, and an artificial lens comprising said fluorine-containing block copolymer.

BRIEF DESCRIPTION OF THE DRAWING

Figure shows the transmittance of the block copolymers prepared in Examples 1 and 2 and PMMA.

DETAILED DESCRIPTION OF THE INVENTION

In the fluorine-containing block copolymer of the present invention, the soft segment comprises chlorotrifluoroethylene (CTFE) and vinylidene fluoride (VdF). A molar ratio of CTFE to VdF is usually from 70:30 to 20:80, preferably from 50:50 to 40:60.

The hard segment comprises a fluorine-containing crystalline polymer. Preferred examples of the fluorine-containing crystalline polymer are a CTFE/ethylene copolymer and a tetrafluoroethylene (TFE)/ethylene copolymer. In the CTFE/ethylene copolymer, a molar ratio of CTFE to ethylene is usually from 80:20 to 50:50, preferably 70:30 to 55:45. In the TFE/ethylene copolymer, a molar ratio of TFE to ethylene is usually from 80:20 to 50:50, preferably from 70:30 to 55:45.

The fluorine-containing block copolymer of the present invention has a weight average molecular weight of 10,000 to 1,000,000, preferably 20,000 to 500,000. The block copolymer of the present invention contains the hard segment in an amount of not larger than 40% by weight. Preferably, a weight ratio of the soft segment to the hard segment is from 90:10 to 80:20.

The block copolymer of the present invention may be prepared by a per se conventional method. For example, a soft segment is polymerized by an iodine-transferring polymerization method which is disclosed in U.S. Pat. No. 4,158,678 the disclosure of which is hereby incorporated by reference. Then, a hard segment is block copolymerized with the soft segment.

The artificial lens of the present invention may be manufactured from the block copolymer of the present invention by a per se conventional method such as press molding or injection molding with using a mold having an interior shape corresponding to the artificial crystalline lens.

The artificial lens of the present invention has flexibility, good transparency and a high refractive index, and absorbs less proteins. It can be inserted in the eye through a small incisure. It can be sterilized in an autoclave. In addition, it absorbs less water.

Properties of PMMA, Daiel Thermo T 530 and the block copolymer of the present invention are shown in Table 1.

TABLE 1

| Polymer | Transparency | Absorbed protein | Incisure (mm) | Refractive index | Sterilization in autoclave |
|---------|--------------|------------------|---------------|------------------|----------------------------|
| PMMA | Good | Much | ca. 7 | High | Impossible |
| T 530 | Good | Few | ca. 3 | Low | Possible |
| Present invention | Good | Few | ca. 3 | High | Possible |

The block copolymer of the present invention can be used not only as the material of the artificial lens which is used for correcting vision of an aphakia which results from evulsion of an opaque lens due to senile cataract, but also as a material of a contact lens. In addition, the block copolymer of the present invention is used as a thermoplastic polymer to produce molded articles such as an O-ring and a tube by utilizing heat resistance, oil resistance, chemical resistance and transparency of the block copolymer.

PREFERRED EMBODIMENTS OF THE INVENTION

The present invention will be illustrated by following Examples.

EXAMPLE 1

In a three liter SUS stainless steel autoclave, pure water (1.5 liters) and an emulsifier (Unidain (trade mark) DS 101 manufactured by Daikin Industries Ltd.) (3 g) were charged. After evacuation while stirring, a monomer mixture of CTFE and VdF in a molar ratio of 45:55 was introduced in the autoclave, and the internal temperature was raised to 70° C. An amount of the monomer mixture was adjusted to keep the internal pressure at 18 kgf/cm$^2$.

Ammonium persulfate (APS) (30 mg) was added to initiate polymerization. As the monomers were consumed, the internal pressure dropped. When the pressure dropped to 17 kgf/cm$^2$, the monomer mixture was again introduced to raise the pressure to 18 kgf/cm$^2$. Simultaneously, I(CH$_2$CH$_2$)$_2$I (0.8844 g) was added. Thereafter, the polymerization was continued while keeping the pressure between 17 and 18 kgf/cm$^2$ by the addition of the monomer mixture till 300 g of the monomer mixture was consumed. A monomer consuming rate was 50 g/hr.

To a resulting emulsion (500 ml), pure water (500 ml) was added and the diluted emulsion was charged in a three liter SUS stainless steel autoclave. After evacuation while stirring, a monomer mixture of CTFE and ethylene in a molar ratio of 72:28 was introduced so that the pressure reached 16 kgf/cm$^2$ when the temperature was raised to 70° C. APS (15 mg) was added to initiate polymerization. The monomer mixture was added to keep the pressure between 15 and 16 kgf/cm$^2$.

An amount of the monomer mixture in the latter step was 15% by weight based on the copolymer contained in the starting emulsion, and the monomer consuming rate was 15 g/hr.

Then, polymerization was stopped by cooling the autoclave. The finally obtained emulsion was coagulated with a 5% aqueous solution of potash alum, and a coagulated material was dried to obtain a white solid copolymer (92 g).

In the obtained block copolymer, a soft segment consisted of a CTFE/VdF copolymer (molar ratio of 45:55), and a hard segment consisted of a CTFE/ethylene copolymer (molar ratio of 72:28). The amount of the hard segment was 15% by weight based on the weight of the soft segment.

EXAMPLE 2

To the emulsion obtained in the first polymerization step in Example 1 (500 ml), pure water (500 ml) was added and the diluted emulsion was charged in a three liter SUS stainless steel autoclave. After evacuation while stirring, a monomer mixture of TFE and ethylene in a molar ratio of 63:37 was introduced so that the pressure reached 16 kgf/cm$^2$ when the temperature was raised to 70° C. APS (15 mg) was added to initiate polymerization. The monomer mixture was added to keep the pressure between 15 and 16 kgf/cm$^2$.

An amount of the monomer mixture in the latter step was 10% by weight based on the copolymer contained in the starting emulsion, and the monomer consuming rate was 12 g/hr.

Then, polymerization was stopped by cooling the autoclave. The finally obtained emulsion was coagulated with a 5% aqueous solution of potash alum, and a coagulated material was dried to obtain a white solid copolymer (90 g).

In the obtained block-copolymer, a soft segment consisted of a CTFE/VdF copolymer (molar ratio of 45:55), and a hard segment consisted of a TFE/ethylene copolymer (molar ratio of 63:37). The amount of the hard segment was 10% by weight based on the weight of the soft segment.

EXPERIMENTS

With PMMA, Daiel Thermo T 530 and the block copolymers prepared in Examples 1 and 2, a BSA absorption amount, an IgG absorption amount, a refractive index, a glass transition temperature and a melting point were measured. The results are shown in Table 2.

The BAS and IgG absorption amounts are measured by preparing a PBS(-) solution of BAS and IgG each in a concentration of one twentieth physiological unit, dipping a film of each polymer for 30 minutes and measuring an absorbed amount of each protein with a BCA assay kit (manufactured by Pias).

TABLE 2

| Polymer | Absorbed amount ($\mu$g/cm$^2$) BSA | IgG | Refractive index | $T_g$ ($T_m$) (°C.) |
|---|---|---|---|---|
| PMMA | 0.373 | 0.782 | 1.49 | 123 |
| T 530 | 0.273 | 0.589 | 1.357 | −9 (253) |
| Example 1 | 0.279 | 0.560 | 1.416 | −6 (247) |
| Example 2 | 0.268 | 0.549 | 1.408 | −8 (252) |

The block copolymers prepared in Examples 1 and 2 absorbed smaller amounts of BSA and IgG and had higher refractive indices. In addition, they had $T_g$ and $T_m$ far away from 100° C., they can be sterilized with steam in an autoclave.

Transparency of PMMA and the block copolymer prepared in Examples 1 and 2 was evaluated.

Each polymer was heat pressed to form a film of 100 $\mu$m in thickness, and transmittance of each film was measured with a spectrophotometer in a wavelength range from 200 to 850 nm. The results are shown in Figure.

As seen from Figure, the block copolymers prepared in Examples 1 and 2 had smaller transmittance than PMMA in the UV light range of 200 to 300 nm, while they had substantially the same transmittance as PMMA in the visible light range. This means that the block copolymer of the present invention can cut the UV light which may be harmful to the eye, while they transmit the visible light in the same transmittance as PMMA.

What is claimed is:

1. An artificial lens sized and configured for insertion into the human eye which comprises a fluorine-containing block copolymer comprising at least one soft segment which comprises chlorotrifluoroethylene and vinylidene fluoride and at least one hard segment which comprises a fluorine-containing crystalline polymer.

2. The artificial lens according to claim 1, wherein a molar ratio of chlorotrifluoroethylene to vinylidene fluoride is from 70:30 to 20:80.

3. The artificial lens according to claim 1, wherein said fluorine-containing crystalline polymer is selected from the group consisting of a chlorotrifluoroethylene and ethylene copolymer and a tetrafluoroethylene and ethylene copolymer.

4. The artificial lens according to claim 3, wherein said fluorine-containing crystalline polymer is a copolymer of chlorotrifluoroethylene and ethylene in a molar ratio of chlorotrifluoroethylene to ethylene of from 80:20 to 50:50.

5. The artificial lens according to claim 3, wherein said fluorine-containing crystalline polymer is a copolymer of tetrafluoroethylene and ethylene in a molar ratio of tetrafluoroethylene to ethylene of from 80:20 to 50:50.

6. The artificial lens according to claim 1, wherein said fluorine-containing block copolymer has a weight average molecular weight of 10,000 to 1,000,000.

7. The artificial lens according to claim 1, wherein a weight ratio of the soft segment to the hard segment is from 90:10 to 80:20.

* * * * *